United States Patent [19]

Eyrisch et al.

[11] Patent Number: 6,072,063
[45] Date of Patent: *Jun. 6, 2000

[54] LOW-MELTING ESTER QUATS

[75] Inventors: Oliver Eyrisch, Burghausen; Rudolf Aigner, Burgkirchen, both of Germany

[73] Assignee: Clariant GmbH, Frankfurt, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/807,868

[22] Filed: Feb. 26, 1997

[30] Foreign Application Priority Data

Mar. 1, 1996 [DE] Germany ............ 196 07 824

[51] Int. Cl.[7] .................................. C07C 101/00
[52] U.S. Cl. ............ 554/110; 554/103; 554/108; 554/109; 564/281; 564/291
[58] Field of Search ............ 554/52, 103, 108, 554/109, 110; 564/281, 291

[56] References Cited

U.S. PATENT DOCUMENTS

| | | | |
|---|---|---|---|
| 5,185,088 | 2/1993 | Artman | 252/86 |
| 5,284,650 | 2/1994 | Whittlinger | 554/103 |
| 5,296,622 | 3/1994 | Uphue et al. | 554/103 |
| 5,463,094 | 10/1995 | Brown et al. | 554/110 |

FOREIGN PATENT DOCUMENTS

| | | |
|---|---|---|
| 1312619 | 1/1993 | Canada. |
| 246133 | 9/1987 | Czechoslovakia. |
| 264073 | 1/1990 | Czechoslovakia. |

OTHER PUBLICATIONS

Chem. abstr. of J. Biopharm. Sci., 2(1), pp. 1–10 showing compounds, 1991.
Chem. abstr., 114:145864, Smidrkal et al., CS 264073, Jan. 1990.
Chem. abstr., Ryzhkov et al., 122:84280, 1995.
Chem. absr., Smidrkal et al., 114:145864, 1991.
Ferdinand Devinsky et al., "Structure–Activity Relationships of 'Soft' Quaternary Ammonium Amphiphiles", Journal of Biopharmaceutical Sciences, Bd. 2, Nr. 1, pp. 1–9 (1991).

Yu. A. Ryzhkov, et al., "Synthesis and Thermal Stability of Cationic Surface–Active Dimethylaminoethanol Derivatives", Russian Journal of Applied Chemistry, vol. 67, No. 5, Part 2, pp. 734–736 —(Nov. 10, 1994).

G. Cerbai et al., "Acetylene derivatives with Antipastic Activity II. Amino Esters of Propylpropargylacetic Acid", Chemical Abstracts, vol. 76, No. 21, May 22, 1972, abstract No. 125937m, p. 413.

V. Majtan et al., "Efficacy of New Organic Ammonium Salts on Pseudomonas Aeruginosa and Salmonella Typhimurium", Arzneimittel Forschung Drug Research, Bd 45, Nr. 2, pp. 198–199 (1995).

Alois Novacek et al., "Preparation of Cationic Surfactants as Antistatic Agents for Textiles", Chemical Abstracts, vol. 108, No. 24, Jun. 13, 1988, Abstract No. 206712r.

*Primary Examiner*—Deborah D. Carr
*Attorney, Agent, or Firm*—Miles B. Dearth

[57] ABSTRACT

Ester quats of the formula (1) below are described:

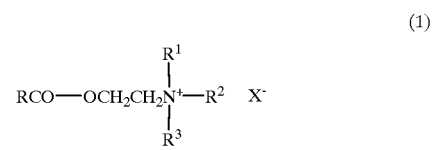

(1)

where RCO is an aliphatic acyl radical having 6 to 22 carbon atoms, $R^1$ is a methyl radical, $R^2$ is a $C_1$–$C_6$-alkyl radical, $R^3$ is a $C_3$–$C_6$-alkyl radical and $X^-$ is a halogen anion. They are prepared by quaternizing the corresponding carboxylic acid ethanolamine ester compound with a methyl halide in the absence or presence of solvents. The ester quats of the invention have a low melting point. Furthermore, even in high concentration they are highly water soluble and, on account of their preparation, are obtained in high purity and free from toxic contents. These ester quats can be used in many ways and are suitable, for example, for preparing solid or aqueous formulations having a high surfactant effect.

13 Claims, No Drawings

LOW-MELTING ESTER QUATS

The invention relates to low-melting quaternary carboxylic acid ethanolamine ester halides, a process for their preparation and their use.

Quaternary carboxylic acid ethanolamine ester salts, also termed ester quats, are highly effective cationic surfactants which can be used in many ways. Thus, these surfactants are suitable, for example, as fabric softeners, cosmetics base materials, active compounds with respect to soil release and soil redeposition, antistatic compositions, fabric finishes, biocide and phase-transfer catalysts. Since these ester quats, owing to their biodegradability, are also ecologically advantageous, they have of late substantially taken over from the classical fatty alkyl quats such as distearyldimethylammonium chloride.

With respect to storage, transport and further processing, ester quats are desired which are already liquid at room temperature or at least have a low melting point. In addition, they should not contain any toxic compounds, and, in particular with regard to further processing to finished formulations, they should also be readily water soluble or water dispersible. Furthermore, a purity as high as possible is desired.

CA-A-1 312 619 describes quaternary ester amines in the form of halides and sulfates which have a low melting point, since they already have a pasty (waxy) consistency at room temperature. However, the low melting point is only achieved by these ester quats containing a greater or lesser amount of glyceride or partial glyceride. The quaternizing agent is an alkyl halide such as methyl chloride or an alkyl sulfate such as dimethyl sulfate. In the latter case, the ester quat/glyceride mixture can also contain toxic dialkyl sulfate. The quaternization, as is verified by all the examples, is carried out in the presence of an organic solvent such as isopropanol.

U.S. Pat. No. 5,463,094 describes quaternary ammonium sulfates and ester amine sulfates. They are prepared in the absence of solvents. The quaternizing agent is dimethyl sulfate which is advantageous (reactive) per se. To avoid toxic residual dialkyl sulfate in the resulting ester quat, the dialkyl sulfate is used in a substoichiometric amount. However, this results in the fact that the ester quat contains a greater or lesser amount of starting compound. Even when its separation and production of pure ester quat compound is possible, this would be complex and costly.

Finally, CS-B-246 133 and CS-B-264 073 may be further mentioned, in which ethanolamine ester sulfates are likewise described. These ester quats, prepared in each case using dimethyl sulfate, also have the abovementioned disadvantages.

Ester quat compounds have now been found which have a low melting point even without the assistance of further components. Furthermore, they are readily water soluble and do not have toxic contents resulting from their preparation. The ester quat compounds of the invention correspond to the following formula (1)

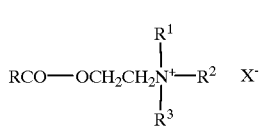

(1)

where

RCO is an aliphatic acyl radical having 6 to 22 carbon atoms, preferably 8 to 18 carbon atoms, $R^1$ is a methyl radical, $R^2$ is a $C_1$–$C_6$-alkyl radical, $R^3$ is a $C_3$–$C_6$-alkyl radical and $X^-$ is a halogen anion.

Preferred ester quats according to the invention of the formula (1) are those where RCO is said acyl radical, $R^1$ is a methyl radical, $R^2$ is a $C_1$–$C_4$-alkyl radical, $R^3$ is a $C_3$ or $C_4$-alkyl radical and $X^-$ is said anion.

Particularly preferred ester quats of the formula (1) have proved to be those where RCO is said acyl radical and $X^-$ is said anion and $R^1$, $R^2$ and $R^3$ are the following alkyl radicals:

$R^1$ methyl, $R^2$ methyl, $R^3$ propyl (ester quat 1a),
$R^1$ methyl, $R^2$ methyl, $R^3$ butyl (ester quat 1b),
$R^1$ methyl, $R^2$ propyl, $R^3$ propyl (ester quat 1c) and
$R^1$ methyl, $R^2$ butyl, $R^3$ butyl (ester quat 1d).

The alkyl radicals mentioned for $R^1$, $R^2$ and $R^3$ can be saturated or unsaturated, linear or branched, saturated and linear being preferred. The halogen anion is preferably $Cl^-$. The aliphatic acyl radical is preferably a fatty acyl radical having said number of carbon atoms. It can be saturated or unsaturated (preferably monounsaturated to triunsaturated). Examples which may be mentioned are the acyl radicals of caprylic, capric, lauric, palmitic, stearic and oleic acids and also coconut acyl, tallow acyl, preferably hardened tallow acyl, and the like. The fatty acid radical is frequently a mixture of two or more acyl groups, for example $C_{12}$ and $C_{14}$-acyl ($C_{12/14}$), $C_{16}$ and $C_{18}$-acyl ($C_{16/18}$) or $C_{12}$ to $C_{18}$-acyl.

The process of the invention for preparing the ester quats of the formula (1) comprises quaternizing a carboxylic acid ethanolamine ester compound of the formula (2) below

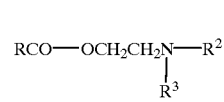

(2)

where RCO, $R^2$ and $R^3$ have the specified meanings, with a methyl halide, preferably with methyl chloride, in the absence of solvents or in the presence of water or a mixture of water and low alkanols as solvent.

In the process of the invention, the quaternization is therefore carried out using said solvents or in the absence of any solvents and using methyl halide as quaternizing agent.

According to a preferred procedure, the esterification is carried out in a first step and the resulting esterification product is then quaternized. In a preferred process therefore
a) an ethanolamine compound of the formula (3) below

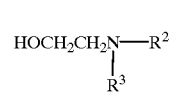

(3)

where $R^2$ and $R^3$ have said meanings, is esterified with a carboxylic acid of the formula (4) below

(4)

where RCO has said meaning,
in the absence of solvents to give the carboxylic acid ethanolamine ester compound and
b) the esterification product obtained in step a) is quaternized as described above.

The process of the invention is described in detail below: the specific ethanolamines of the formula (3) or ethanolamine esters of the formula (2) to be used are given by the meanings specified under formula (1) for $R^2$, $R^3$ and RCO. The same applies to the carboxylic acid (fatty acid) to be used of the formula (4). The ethanolamine compound and carboxylic acid are reacted to form the ester compound in the absence of organic or other solvents. The temperature of the esterification reaction is 100 to 250° C., preferably 130 to 200° C. The reaction components ethanolamine of the formula (3) and carboxylic acid of the formula (4) are used in a molar ratio of 0.8 to 1.2 mol of carboxylic acid, preferably 1 to 1.05 mol of carboxylic acid, per mole of ethanolamine. Esterification catalysts can be used to accelerate the esterification reaction. Preference is given to acid catalysts, more precisely hydrohalic acids such as hydrochloric acid; phosphorus acids such as hypophosphorous acid or orthophosphoric acid; sulfuric acid and sulfonic acids such as methanesulfonic acid, paratoluenesulfonic acid or dodecyl benzenesulfonic acid. Preference is given to phosphorus acids and sulfonic acids. The amount of acid catalyst is generally 0.05 to 0.5% by weight, based on the weight of the ethanolamine used. Depending on the reaction temperature and type of reaction components, the reaction will proceed at atmospheric pressure or under the pressure which establishes itself. It is preferred to maintain an inert gas atmosphere, for example a nitrogen atmosphere, during the reaction. It is further preferred to remove the reaction water from the reaction mixture, for example using an inert gas stream and/or vacuum. The esterification reaction is expediently followed by gas-chromatographic analysis or by determining the acid number. The reaction time is generally in the range from 5 to 15 hours. The esterification product obtained, which, if appropriate, is washed with water, is liquid to waxy at room temperature and essentially comprises the desired carboxylic acid ethanolamine ester compound according to formula (2).

The quaternization reaction of the process according to the invention is preferably carried out on the ester amine product obtained using the above described esterification reaction. Ester amine products of the formula (2) which are obtained in other ways or are commercially available can also be used. The quaternization is carried out using a methyl halide in the absence of solvents or in the presence of said solvents, in the first case (reaction in the absence of solvents), a temperature of 50 to 200° C., preferably 60 to 150° C., being maintained, and in the second case (reaction in the presence of a solvent) a temperature of 40 to 100° C., preferably 50 to 80° C., being maintained. In the water/alkanol mixture as solvent, the proportion of alkanol can vary within wide limits. It is generally 0 to 70% by weight of alkanol, preferably 3 to 20% by weight, percentages by weight based on the mixture of water and alkanol. Preferred low alkanols are the $C_1$–$C_4$-alkanols such as methanol, ethanol, propanol and isopropanol. Clearly, the quaternization can be carried out at relatively low temperatures, owing to the resulting low-melting ester quats. Owing to the further special property of these structurally selected compounds, that is to say their ready water solubility, the quaternization can also be carried out with concentrated to highly concentrated aqueous product compositions using water alone as solvent. It is thus possible to carry out this quaternization using an amount of solvent (for example amount of water) of less than 45% by weight, preferably 5 to 25% by weight, percentages by weight based on the solution. The ester amine to be quaternized is brought together, as such or in the form of said solutions, with the gaseous methyl halide, which is preferably methyl chloride, the methyl halide being used in an amount (primarily for safety reasons) such that a maximum pressure of 10 bar is present, preferably 2 to 8 bar. It is expedient to follow the quaternization reaction by continuous determination of the degree of quaternization. The reaction time is generally 5 to 15 hours. The end of the quaternization is clear from the pressure which no longer decreases and remains constant. The excess methyl halide is simply removed by pressure reduction and, if appropriate, evacuation. The resulting ester quats which are waxy at room temperature have a melting point of at most 80° C., generally at most 70° C., at which they are readily flowable (pourable).

The process of the invention can be carried out either batchwise or else continuously. The continuous procedure is preferably carried out in at least two, preferably two to three, stirred tanks arranged in cascade. It is advantageous here to feed ester amine and methyl halide continuously to the first tank, after a conversion rate of ester amine and methyl halide of about 10 to 30 mol %, based on ester amine, is achieved, and to set the residence time of the product composition in the stirred tanks such that the product from the last tank has the desired degree of quaternization.

The quaternization according to the invention using a methyl halide has, in comparison with that using a dialkyl sulfate, the great advantage that the quaternizing agent can also be used in excess without problems, since methyl halides, in contrast to dialkyl sulfates, can be removed readily and quantitatively from the reaction product. With the methyl halide excess which can be used without problems, as a further advantage, an increased reaction rate and a high degree of conversion are achieved. The quaternary ester amine halides of the invention have an unexpectedly low melting point, and they have this even in the absence of auxiliaries, additives, solvents and the like which depress melting points. Furthermore they exhibit good water solubility and biodegradability and, on account of their special mode of preparation, can be obtained in high purity and free of toxic contents and organic solvent residues. The novel low-melting cationic surfactants can also be provided as highly concentrated aqueous solutions (for example even containing 90% by weight of active compound), which, despite the high active compound concentration, are readily flowable even at room temperature (15 to 25° C.). On account of these outstanding properties, the ester quats of the invention are suitable particularly advantageously anywhere where cationic surfactants are desired, for example in all fields of application mentioned at the outset. Their use according to the invention is preferably in the preparation of aqueous formulations having a high surfactant effect. The novel ester quats are also advantageously suitable for preparing solid formulations. In this case, the starting point is the molten state of the novel products of the invention or their solutions and the melts or the solutions are subjected to conventional manufacturing processes for converting the product into a solid form such as powder, pellets, granules and the like. Processes of this type are, for example, spray-cooling or spray-granulation in the case of melts and agglomeration or spray-drying in the case of solutions. If appropriate, auxiliaries can be used to manufacture the formulations.

The invention is now described in more detail on the basis of examples and comparison examples.

EXAMPLE 1

N,N-Dipropyl-N-methyl-[1-oxododecyl(tetradecyl)oxyethyl]-ammonium chloride 612 g (3 mol) of lauric acid and 445 g (3 mol) of dipropylethanolamine are charged in a three-neck flask equipped with thermometer, agitator and bridge-shaped still head and are heated to 160° C. internal temperature with nitrogen flushing. After a post-reaction period of 2 hours at 160° C., the mixture is heated to 190° C. in the course of one hour. In the course of further stirring for 10 hours at 190° C., residual reaction water distills over. In this manner, 1003 g of a yellowish oil are obtained (amine number 29.8 ml of 0.1 N HCl/g).

204 g (0.6 mol) of the ester amine thus obtained are charged to a 1 liter pressure glass autoclave. The closed autoclave is heated to 120° C. and then, a little at a time, just enough methyl chloride is added so that the pressure does not exceed 5 bar. After stirring for 7 hours at 120° C. and 4 to 5 bar, the pressure is reduced and physically dissolved methyl chloride is removed by evacuation (200 mbar). In this manner, 234 g of the desired quaternary ammonium compound are obtained in the form of a weakly yellowish solid (melting point 69° C., cationic active substance 2.53 mmol of N/g, purity 95%.

EXAMPLE 2
N,N-Dibutyl-N-methyl-[1-oxododecyl(tetradecyl) oxyethyl]-ammonium chloride 172 g (0.85 mol) of lauric acid and 145 g (0.85 mol) of dibutylethanolamine are charged in a three-necked flask equipped with thermometer, agitator and bridge-shaped still head and are heated to 160° C. internal temperature with nitrogen flushing. After a post-reaction time of 1 hour at 160° C., the mixture is heated to 190° C. in the course of 30 minutes. In the course of stirring at 190° C. for a further 8 hours, residual reaction water distills over. In this manner, 302 g of a yellowish oil are obtained (amine number 27.6 ml of 0.1 N HCl/g).

249 g (0.69 mol) of the ester amine thus obtained are charged in a 1 liter pressure glass autoclave. The closed autoclave is heated to 75 to 80° C. and then, a little at a time, just enough methyl chloride is added so that the pressure does not exceed 5 bar. After stirring for 12 hours at 80° C. and 4 to 5 bar, the pressure is reduced and physically dissolved methyl chloride is removed by evacuation (200 mbar). In this manner, 283 g of the desired quaternary ammonium compound are obtained in the form of a weakly yellowish solid (melting point 54° C. cationic active substance 2.37 mmol of N/g, purity 95%).

EXAMPLE 3
N,N-Dipropyl-N-methyl-[1-oxododecyl(tetradecyl) oxyethyl]-ammonium chloride 286 g (0.85 mol) of the ester amine from Example 1 are charged in a 1 liter pressure glass autoclave together with 36.5 g of water. The closed autoclave is heated to 60° C. and then, a little at a time, just enough methyl chloride is added so that the pressure does not exceed 5 bar. After stirring for 9 hours at 60° C. and 4 to 5 bar, the pressure is reduced and physically dissolved methyl chloride is removed by evacuation (200 mbar). In this manner, 361 g of the desired quaternary ammonium compound are obtained in the form of a weakly yellowish pourable syrup (solids content 90%, purity 93%).

COMPARISON EXAMPLE 1
N,N,N-Trimethyl-[1-oxododecyl(tetradecyl)oxyethyl]-ammonium chloride 1.15 kg (5.6 mol) of lauric acid are charged in a three-neck flask equipped with thermometer, agitator and bridge-shaped still head, heated to 160° C. internal temperature with nitrogen flushing and 645 g (7 mol) of dimethylethanolamine are added dropwise continuously in the course of 6 hours. After a post-reaction time of 2 hours at 160° C., the mixture is heated to 180° C. in the course of 30 minutes. During stirring for a further 3 hours at 180° C., residual reaction water distills over. To remove the excess amine, the mixture is further stirred for 3 more hours at a pressure of 30 mbar. In this manner, 1.56 kg of a yellowish oil are obtained (amine number 33.3 ml of 0.1 N HCl/g).

365 g (1.2 mol) of the ester amine thus obtained are charged in a 1 liter pressure glass autoclave together with 74 g of isopropanol. The closed autoclave is heated to 75 to 80° C. and then, in the course of 2 hours, a little at a time just enough methyl chloride is added so that the pressure does not exceed 5 bar. After stirring for 6 hours at 80° C. and 4 to 5 bar, the pressure is reduced and physically dissolved methyl chloride is removed on a rotary evaporator (80° C./200 mbar). The desired quaternary ammonium compound is obtained in this manner in the form of an 85% strength isopropanol-moist weakly yellowish residue (melting point 53° C., cationic active substance 2.12 mmol of N/g, purity 97%, based on the dry residue). A portion of the product is dried in a vacuum drying cabinet (100° C./100 mbar). A powder which melts with decomposition at 173° C. is thus obtained.

COMPARISON EXAMPLE 2
N,N-Diethyl-N-methyl-[1-oxododecyl(tetradecyl) oxyethyl]-ammonium chloride 612 g (3 mol) of lauric acid are charged in a three-neck flask equipped with thermometer, agitator and bridge-shaped still head, heated to 160° C. internal temperature with nitrogen flushing and 439 g (3.75 mol) of diethylethanolamine are continuously added dropwise in the course of 5 hours. After a post-reaction time of 2 hours at 160° C., the mixture is heated to 180° C. in the course of 30 minutes. During stirring for a further 8 hours at 180° C., residual reaction water distills over. To remove the excess amine, the mixture is further stirred for 3 more hours at a pressure of 20 mbar. In this manner, 909 g of a yellowish oil are obtained (amine number 32.4 ml of 0.1 N HCl/g).

371 g (1.2 mol) of the ester amine thus obtained are charged in a 1 liter pressure glass autoclave together with 76 g of isopropanol. The closed autoclave is heated to 75 to 80° C. and then, in the course of 2 hours, a little at a time, just enough methyl chloride is added so that the pressure does not exceed 5 bar. After stirring for 6 hours at 80° C. and 4 to 5 bar, the pressure is reduced and physically dissolved methyl chloride is removed on a rotary evaporator (80° C./200 mbar). The desired quaternary ammonium compound is obtained in this manner in the form of an 85% strength isopropanol-moist weakly yellowish residue (melting point 53° C., cationic active substance 2.36 mmol of N/g, purity 99%, based on the dry residue). A portion of the product is dried in a vacuum drying cabinet (100° C./100 mbar). A powder which melts with decomposition at 155° C. is obtained.

COMPARISON EXAMPLE 3
N,N-Dioctyl-N-methyl-[1-oxododecyl(tetradecyl) oxyethyl]-ammonium chloride 36.4 g (0.18 mol) of lauric acid and 49 g (0.18 mol) of dioctylethanolamine are charged in a three-neck flask equipped with thermometer, agitator and bridge-shaped still head and heated to 160° C. internal temperature with nitrogen flushing. After a post-reaction time of 1 hour at 160° C., the mixture is heated to 190° C. in the course of 30 minutes. During stirring for a further 11 hours at 190° C., residual reaction water distills over. In this manner, 82 g of a yellowish oil are obtained (amine number 20.7 ml of 0.1 N HCl/g).

50 g (0.1 mol) of the ester amine thus obtained are charged in a 1 liter pressure glass autoclave together with 13.8 g of isopropanol. The closed autoclave is heated to 75 to 80° C. and then, in the course of 2 hours, a little at a time, just enough methyl chloride is added so that the pressure does not exceed 5 bar. After stir-ring for 3 days at 80° C. and 4 to 5 bar, the pressure is reduced and physically dissolved methyl chloride is removed on a rotary evaporator (80° C./200 mbar). The desired quaternary ammonium compound is obtained in this manner as an 85% strength mixture in isopropanol in the form of a weakly yellowish oil (cationic active substance 1.62 mmol of N/g, purity 92%, based on the dry residue). A portion of the product is dried in a vacuum drying cabinet (100° C./100 mbar). A solid which melts at 93 to 95° C. is obtained.

COMPARISON EXAMPLE 4

N-Methyl-[1-oxododecyl(tetradecyl)oxyethyl]morpholinium chloride 652 g (3.2 mol) of lauric acid and 417 g (3.2 mol) of hydroxyethylmorpholine are charged in a three-neck flask equipped with thermometer, agitator and bridge-shaped still head and heated to 160° C. internal temperature with nitrogen flushing. After a post-reaction time of 1 hour at 160° C., the mixture is heated to 190° C. in the course of 30 minutes. During stirring for a further 29 hours at 190° C., residual reaction water distills over. In this manner, 1012 g of a yellowish oil are obtained (amine number 30.8 ml of 0.1 N HCl/g).

195 g (0.6 mol) of the ester amine thus obtained are charged in a 1 liter pressure glass autoclave together with 72 g of isopropanol. The closed autoclave is heated to 75 to 80° C. and then, in the course of 2 hours, a little at a time, just enough methyl chloride is added so that the pressure does not exceed 5 bar. After stirring for 38 hours at 80° C. and 4 to 5 bar, the pressure is reduced and physically dissolved methyl chloride is removed on a rotary evaporator (80° C./200 mbar). The desired quaternary ammonium compound is obtained in this manner as an 80% strength mixture in isopropanol in the form of a weakly yellowish oil (cationic active substance 2.05 mmol of N/g, purity 94%, based on the dry residue). A portion of the product is dried in a vacuum drying cabinet (100° C./100 mbar). A solid which melts above 150° C. is obtained.

What is claimed is:

1. A process for preparing a quaternary carboxylic acid ethanolamine ester halide having a melting point of at most 80° C. and having the formula (1):

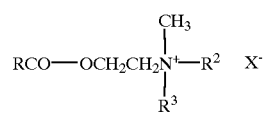

(1)

wherein

RCO is an aliphatic acyl radical having 8 to 18 carbon atoms, $R^2$ is a $C_3$ to $C_6$-alkyl radical, $R^3$ is a $C_3$–$C_6$ alkyl radical, and $X^-$ is halogen, said process comprises quaternizing a carboxylic acid ethanolamine ester with a quaternizing agent consisting of methyl halide, said carboxylic acid ethanolamine ester has the formula (2)

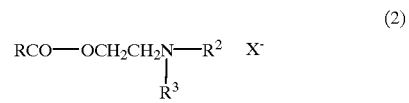

wherein

RCO is an aliphatic acyl radical having 8 to 18 carbon atoms, $R^2$ is a $C_3$–$C_6$ alkyl radical, and $R^3$ is a $C_3$–$C_6$ alkyl radical, said quaternizing is carried out in the absence of organic solvents other than water, or in the presence of water, or in the presence of mixtures of water and low alkanol.

2. The process as claimed in claim 1 wherein (a) ethanolamine of the formula (3) below

where $R^2$ is a $C_1$–$C_6$-alkyl radical, and $R^3$ $C_3$–$C_6$-alkyl radical is esterified with a carboxylic acid of the formula (4): RCO—OH, where RCO is an aliphatic acyl radical having 6 to 22 carbon atoms, in the absence of solvents to give the carboxylic acid ethanol amine ester compound, and (b) the esterification product obtained in step a) is quaternized with said methyl halide in the absence of solvents or in the presence of water or a mixture of water and low alkanols as solvent.

3. The process as claimed in claim 1, wherein the quaternization is carried out in the presence of water and 0 to 70% by weight of a low alkanol as solvent, percentages by weight based on the mixture of water and alkanol, and using an amount of solvent of less than 45% by weight, based on the product solution.

4. The process as claimed in claim 1, wherein the quaternization is carried out with methyl chloride.

5. The process as claimed in claim 1, wherein the quaternization is carried out in the absence of solvents at a temperature of 50° C. to 200° C. and the quaternization in the presence of solvents is carried out at a temperature of 40° C. to 100° C.

6. The process as claimed in claim 1, wherein the quaternization is carried out continuously in at least two stirred tanks arranged in cascade.

7. The process as claimed in claim 2, wherein the temperature of the esterification is from 100° C. to 250° C. and the molar ratio of formula (3) to formula (4) is from 0.8 to 1.2 mol of carboxylic acid per mole of ethanolamine.

8. The process as claimed in claim 7, wherein the esterification temperature is from 130° C. to 200° C. and the molar ratio of formula (3) to fromula (4) is 1 to 1.05 mol of carboxylic acid per mole of ethanolamine.

9. The process as claimed in claim 8, wherein the quaternization is carried out in the absence of solvents at a temperature of 60° C. to 150° C. and the quaternization in the presence of solvents is carried out at a temperature of 50° C. to 80° C.

10. The process of claim 1 wherein $R^1$ is methyl, $R^2$ is methyl and $R^3$ is propyl, or $R^1$ is methyl, $R^2$ is methyl and $R^3$ is butyl, or $R^1$ is methyl, $R^2$ is propyl and $R^3$ is propyl, or $R^1$ is methyl, $R^2$ is butyl and $R^3$ is butyl, and $X^-$ is Cl.

11. The process of claim 1 wherein said quaternary carboxylic acid ethanolamine ester halide is N,N-dibutyl-N-methyl-[1,-oxododecyl(tetradecyl)oxyethyl]-ammonium chloride.

12. The process of claim 1 wherein said quaternary carboxylic acid ethanolamine ester halide is N,N-dipropyl-N-methyl-[1,-oxododecyl(tetradecyl)oxyethyl]-ammonium chloride.

13. The process of claim 1 wherein said quaternary carboxylic acid ethanolamine ester halide is N,N,N-dimethylpropyl-[1-oxododecyl(tetradecyl)oxyethyl]-ammonium chloride.

* * * * *